United States Patent [19]

Borris et al.

[11] Patent Number: 4,814,324

[45] Date of Patent: Mar. 21, 1989

[54] STEROL INHIBITORS OF TESTOSTERONE 5α-REDUCTASE

[75] Inventors: Robert P. Borris, East Brunswick; Richard W. Burg, Murray Hill; Otto D. Hensens, Red Bank; Leeyuan Huang, Watchung; Livia Kelemen, Clark, all of N.J.; Sagrario Mochales, Madrid, Spain

[73] Assignee: Merck & Co., Inc., Rahway, N.J.

[21] Appl. No.: 23,015

[22] Filed: Mar. 6, 1987

[51] Int. Cl.$^4$ .................... A61K 31/56; C07C 167/18
[52] U.S. Cl. .......................................... 514/26; 536/5; 435/52; 435/53; 435/911
[58] Field of Search ............... 514/26; 536/5; 435/52, 435/53, 149, 911

[56] References Cited

U.S. PATENT DOCUMENTS

| | | | |
|---|---|---|---|
| 3,010,878 | 11/1961 | Pan et al. | 435/52 |
| 3,475,275 | 10/1969 | Shirasaka et al. | 435/53 |
| 3,507,749 | 4/1970 | Sih | 435/53 |
| 3,578,565 | 5/1971 | Schocher et al. | 435/911 |
| 3,892,629 | 7/1975 | Smith et al. | 435/137 |
| 4,088,760 | 5/1978 | Benson et al. | 514/177 |
| 4,188,379 | 2/1980 | Pegel | 536/5 |
| 4,396,615 | 8/1983 | Petrow et al. | 514/177 |

FOREIGN PATENT DOCUMENTS

| | | | |
|---|---|---|---|
| 0691119 | 7/1964 | Canada | 435/911 |
| 0767422 | 2/1957 | United Kingdom | 435/911 |

*Primary Examiner*—Ronald W. Griffin
*Assistant Examiner*—Nancy S. Carson
*Attorney, Agent, or Firm*—Hesna J. Pfeiffer; Charles M. Caruso

[57] ABSTRACT

The compounds of Formula I are produced by the aerobic fermentation of a fungus of the genus GLIOCLADIUM, ATCC No. 20826.

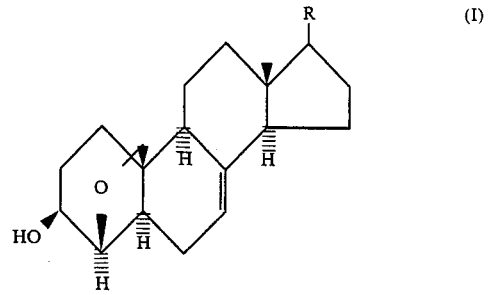

The compounds of Formula I are inhibitors of testosterone 5α-reductase and are useful in the treatment and prevention of acne, seborrhea, female hirsutism and benign prostatic hypertrophy.

6 Claims, 2 Drawing Sheets

STEROL INHIBITORS OF TESTOSTERONE 5α-REDUCTASE

BACKGROUND OF THE INVENTION

The present invention pertains to the novel compounds of Formula I and the use of such compounds as testosterone-5α-reductase inhibitors.

It is well known in the art that certain undesirable physiological manifestations, such as acne vulgaris, seborrhea, female hirsutism, male pattern baldness and benign prostatic hypertrophy, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethylisobutyranilide. See Neri et al., Endo. 2 (1972). However, these products, though devoid of hormonal effects, are peripherally active, competing with the natural androgens for receptor sites, and hence have a tendency to feminize a male host or the male fetus of a female host.

It more recently became known in the art that the principal mediator of androgenic activity in some target organs is 5α-dihydrotestosterone, and that it is formed locally in the target organ by the action of testosterone-5α-reductase. It therefore has been postulated and demonstrated that inhibitors of testosterone-5α-reductase will serve to prevent or lessen symptoms of hyperandrogenic stimulation. Nayfeh et al , Steroids, 14, 269 (1969) demonstrated in vitro that methyl 4-androsten-3-one-17β-carboxylate was a testosterone-5α-reductase inhibitor. Then Voigt and Hsia, Endocrinology, 92, 1216 (1973), Canadian Pat. No. 970,692, demonstrated that the above ester and the parent free acid, 4-androsten-3-one-17β-carboxylic acid are both active inhibitors of testosterone-5α-reductase in vitro. They further demonstrated that topical application of either testosterone or 5α-dihydrotestosterone caused enlargement of the female hamster flank organ, an androgen dependent sebaceous structure. However, concomitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone-5α-reductase.

Recently, a number of investigators have published regarding the biological activity of 5α-reductase inhibitors. See for example, Brooks, et al., The prostate 9: 65–75 (1986), Liang et al., Endrocrinology 117, No. 2, pp. 571–579 (1985), Rasmusson et al., J. Med. Chem. 27: 1690–1701 (1984), Liang et al., J. Biol. Chem. 259, No. 2, pp 734–739 (1984). However, the compounds of the present invention have quite distinct structures from those previously reported for testosterone-5α-reductase inhibitors.

The compounds of Formula I are sterol inhibitors of testosterone-5α-reductase. While 4,19-oxygen bridged cholestanes have been reported in the literature [F. Turecek and P. Kocovsky, Coll. Czech. Chem. Comm. 45, 274–293 (1980); P. Kocovsky, Coll. Czech. Chem. Cmmun. 45, 3008–3022 (1980)], these compounds are not sterols nor are they shown to be inhibitors of 5α reductase.

BASIC DESCRIPTION OF THE DRAWINGS

SUMMARY OF THE INVENTION

Figure 1:
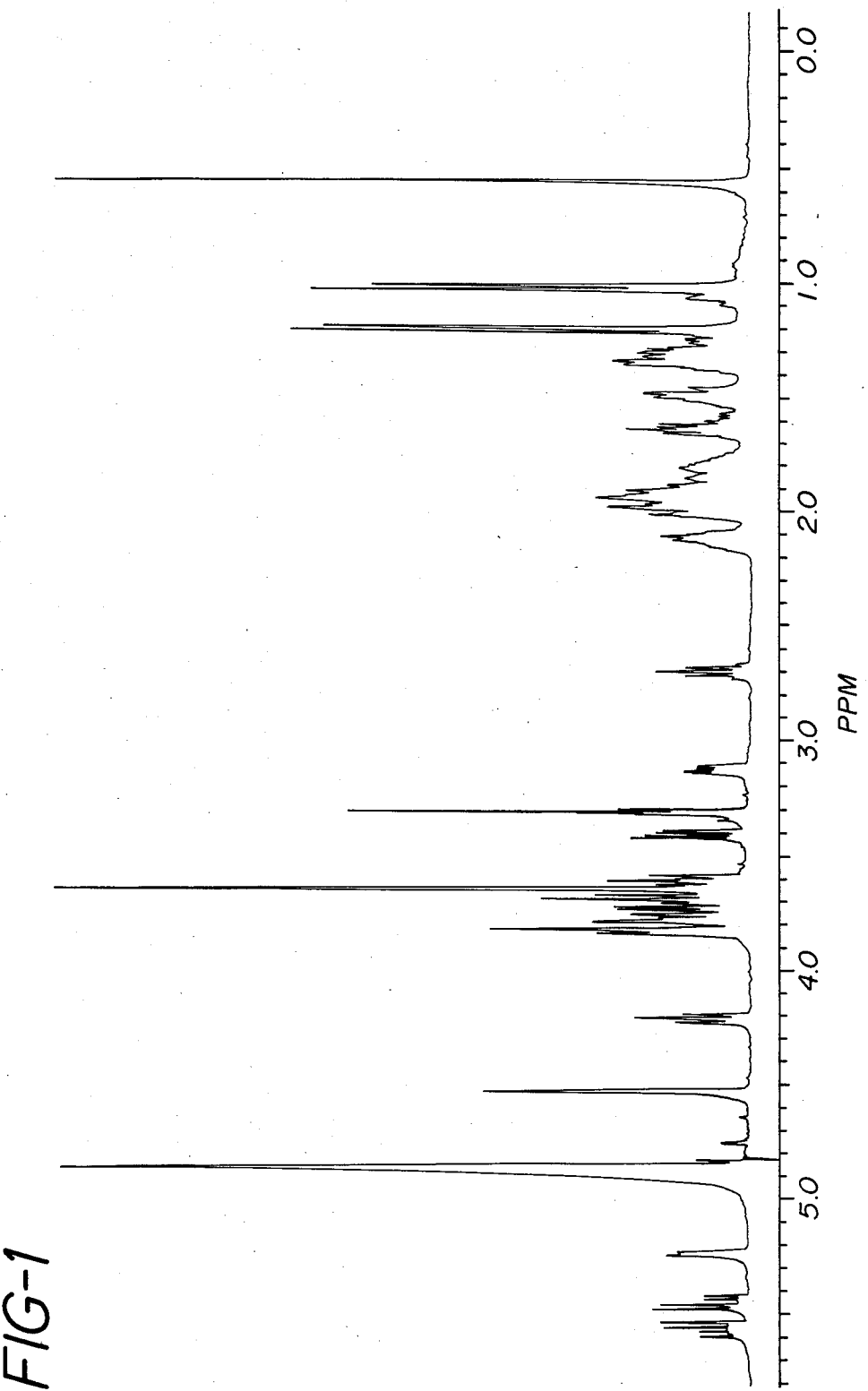
FIG. 1 is a proton nuclear magnetic resonance ($^1$H-NMR) spectrum of compound Ia.

The compounds of Formula I are produced by the controlled aerobic fermentation of the genus GLIOCLADIUM, ATCC No. 20826.

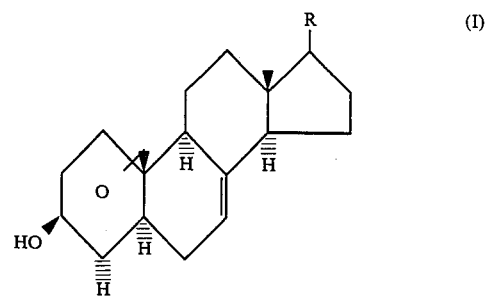

wherein R is

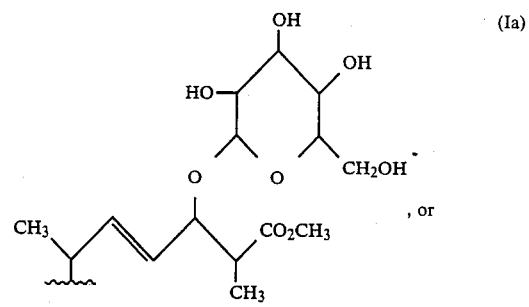

, or

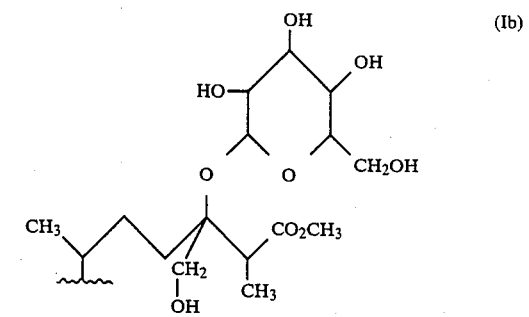

The compounds of Formula I are inhibitors of testosterone 5α-reductase and are useful in the treatment and prevention of acne, seborrhea, female hirsutism and benign prostatic hypertrophy.

The preparation and isolation of the compounds of Formula I is described. Also described is the in vitro activity of the compounds of Formula I as inhibitors of testosterone-5α-reductase.

DETAILED DESCRIPTION OF THE INVENTION

The compounds of Formula I are produced by the controlled aerobic fermentation of a fungus of the genus GLIOCLADIUM.

The fungus ATCC No. 20826 was isolated from a soil sample from Mexico. A deposit under the provisions of the Budapest Treaty of a biologically pure culture of this microorganism was made on Dec. 17, 1986 with the American Type Culture Collection, Rockville, Md. from which it is available under accession number ATCC No. 20826.

An examination of the cuttural and morphological characteristic of the genus GLIOCLADIUM was made. The results are as follows:

Morphological Characteristics

Conidiophores are septate, penicillately branched, generally asymmetrical, and form a single, gelatinous, dark-colored head in which chains of conidia are not distinguishable. Individual conidia are hyalin, elliptical to oviform, generally 2.4 microns by 4.8 to 6.0 microns, borne from tips of sterigmata and forming large balls of conidia enveloped in slime. In young cultures a few chains of mucilaginous conidia may be found but the dominant feature is the large slime ball which forms over adjacent sterigmata on a single conidiophore and coalesces into larger masses where several conidiophores are close together.

Cultural Characteristics

Colonies on Czapek-Dox agar, potato dextrose agar, yeast extract-malt extract agar and Saboraud maltose agar are broadly spreading, velvety, with abundant aerial mycelia, white at first, becoming sand-colored to yellowish-tan as colony ages. Reverse is tan-colored.

Fermentation Conditions:

The compounds of Formula I are produced by the aerobic fermentation of suitable aqueous nutrient media under controlled conditions via inoculation with a culture of the genus GLIOCLADIUM, ATCC No. 20826. The media contains sources of assimilable carbon, nitrogen, and inorganic salts. In general, carbohydrates (for example, glucose, fructose, maltose, sucrose, xylose, and the like) can be used either alone or in combination as sources of assimilable carbon in the nutrient medium. These carbon sources may be used individually or combined in the medium.

Generally, many proteinaceous materials may be used as nitrogen sources for the fermentation process. Suitable nitrogen sources include, for example, yeast hydrolysates, primary yeast, soybean meal, cottonseed meal, hydrolysates of casein, cornsteep liquor, distillers solubles or tomato paste, and the like.

Among the nutrient inorganic salts that can be incorporated into the culture medium are customary salts capable of yielding sodium, potassium, ammonium, calcium, phosphate, sulfate, chloride, carbonate, and similar ions. Also included are trace metals such as cobalt, manganese, iron, magnesium, and the like.

It should be noted that the nutrient medium described herein are merely illustrative of the wide variety of media which may be employed, and are not intended to be limiting.

The fermentation is carried out at temperatures ranging from about 20° C. to 37° C.; the pH of the nutrient medium for growing of the genus GLIOCLADIUM, ATCC No. 20826, cultures and producing the compounds of Formula I can vary from about 6.8 to 7.4.

It is to be understood that for the fermentation production of the compounds of Formula I, the present invention is not limited to the use of the genus GLIOCLADIUM, ATCC No. 20826. It is especially desired and intended that there be included within the scope of this invention, the use of other natural or artificial mutants produced or derived from the described cultures, or other variants or species of the genus GLIOCLADIUM in so far as they can produce the compounds of Formula I. The artificial production of mutant species or strains from ATCC No. 20826 may be achieved by conventional physical or chemical mutagens, for example, ultraviolet irradiation of the desired cultures, or nitrosoguanidine treatment and the like. Recent recombinant DNA techniques such as protoplast fusion, plasmid incorporation, chromosome fragment incorporation and the like may also prove useful.

In a preferred embodiment of the present invention, the compounds of Formula I are produced by the controlled aerobic fermentation of the genus GLIOCLADIUM, ATCC No. 20826. The fermentation should be conducted at a temperature range of from about 20° to 37° C., preferably at about 28° C. Generally, the composition of the assimilable nutrient medium may be varied over a wide range. The essential nutrient ingredients are a carbon source and a nitrogen source. Other essential nutrients are provided via mineral salts such as the chlorides, nitrates, sulfates, carbonates and phosphates of sodium, potassium, ammonium and calcium. The nutrient medium may also contain sources of inorganic trace elements such as magnesium, iron, copper, manganese, zinc, cobalt and the like.

Typical sources of carbon include; glucose, oils, organic acids, dextrin, starches, glycerol and the like. Typical nitrogen sources include; amino acids, vegetable meals, and extracts (e.g., malts, soy, cotton seed, figs, tomato, corn, etc.), animal viscera, various hydrolysate (e.g., casein, yeast, etc.) and industrial by-products such as lard water and distillers solubles.

The maximum yield of the compounds of Formula I can be achieved within about 24 to 200 hours, usually in about 96–144 hours, of fermentation under optimum conditions. The inoculum for the fermentation may be provided from vegetative growth in a medium which supports rapid growth of the microorganism, or directly from spores.

Following fermentation, the accumulated compounds of Formula I may be separated from related compounds and recovered from the broth by conventional chromatographic means.

Adsorption and partition chromatographies, gel filtration, reversed-phase liquid chromatography and the like may be used, in conjunction with eluents of proper polarity and solubilizing characteristics to afford the compounds of Formula I.

A number of different nutrient media may be employed in the fermentation of of the genus GLIOCLADIUM, ATCC No. 20826. Variation of the medium or the microorganism will vary the yield of the compound of Formula I and/or its rate of production. Variation of the medium or the microorganism may also increase or decrease the type and amount of the compounds present in the broth. The preferred media compositions are set forth in Table I.

TABLE I

| KF | |
|---|---|
| Corn Steep | 5 gm |
| Tomato Paste | 40 gm |
| Oatmeal | 10 gm |
| Cerelose | 10 gm |
| Trace Element No. 2 | 10 ml |
| Distilled Water | 1000 ml |
| pH = 6.8 | |

| F 842 | Amount 250 ml flask |
|---|---|
| Corn | 10 gm |
| Salt Solution A | 15 ml |
| Glycerol | 1 ml |
| Yeast Extract | 0.5 gm |
| Corn Oil | 0.1 ml |
| Autoclave, add distilled water per flask, reautoclave | 15 ml |

| Salt Solution A | |
|---|---|
| $MgSO_4.7H_2O$ | 0.1 g |
| Na Tartrate | 0.1 g |
| $FeSO_4.7H_2O$ | 0.01 g |
| $ZnSO_4.7H_2O$ | 0.01 g |
| Distilled water | 1000 ml |

| Trace Element No. 2 | |
|---|---|
| $FeSO_4.7H_2O$ | 1000 mg |
| $MnSO_4.4H_2O$ | 1000 mg |
| $CuCl_2.2H_2O$ | 25 mg |
| $CaCl_2$ | 100 mg |
| $H_3BO_3$ | 56 mg |
| $(NH_4)_6MoO_2.4H_2O$ | 19 mg |
| $ZnSO_4.7H_2O$ | 200 mg |
| Distilled Water | 1000 ml |

| YME | |
|---|---|
| Yeast Extract | 4.0 g |
| Malt Extract | 10.0 g |
| Dextrose | 4.0 g |
| Agar | 20.0 g |
| Distilled Water | 1000 ml |
| pH = 7.0 | |

The terms "seed" and "production" media are employed as terms of art. Generally, a seed medium supports rapid growth of the microorganism and an aliquot (seed) of this medium is used to inoculate a production medium for a large scale fermentation.

The following examples describe the fermentation isolation of the compounds of its several minor related compounds. These examples are merely illustrative, they are not intended to limit the scope of this invention.

EXAMPLE 1

A portion of the surface growth from an agar slant of a culture of ATCC No. 20826, was inoculated into 54 ml of KF seed media in 250 ml Erlenmeyer flask. This seed was incubated at 25° C., 220 rpm for three days. An inoculum was then used to inoculate a 250 ml Erlenmeyer flask containing solid production media, F842. The production flasks were incubated at 28° C., 220 rpm for 14 days. After this time, 40 ml of 40% acetone or 40 ml of 50% methanol were added to each flask to break up the solid growth pad and the flasks were harvested.

EXAMPLE 2

The solid fermentation product from Example 1 (nominally 6 liters total) was dispersed in acetone:water (3:2 v/v, 6 L) and stirred overnight. The resulting mixture was then filtered, and the filtrate evaporated to dryness. The residue was dispersed in water (2 L) and extracted with 3 successive portions of water-saturated n-butanol (2 L each). The pooled organic phase was evaporated to dryness, then the residue was dissolved in methanol:water (9:1 v/v, 2 L) and defatted with 3 successive portions of n-hexane (2 L each). The defatted methanol fraction was evaporated, the residue redissolved in methanol:water (9:1 v/v, 300 ml) and extracted with 4 successive portions of n-hexane (300 ml each). The hexane-depleted methanol fraction was evaporated to dryness, then dispersed in water (300 ml) and extracted successively with ethyl acetate (4 portions, 300 ml each) and water-saturated n-butanol (4 portions, 300 ml each). The organic phases were pooled and evaporated. The resulting residue was triturated with acetonitrile (500 ml) and filtered. The filter cake was washed with acetonitrile, then the pooled filtrate and wash were extracted with n-hexane (5 portions, 250 ml each) and evaporated to dryness, affording an active residue. The acetonitrile-insoluble filter cake was dispersed in methanol and filtered. Upon evaporation of the filtrate, an active residue was afforded.

Gel filtration of the acetonitrile-soluble fraction was performed on Sephadex LH-20 (Pharmacia Fine Chemicals) in methanol. The sample was applied in minimal volume of methanol to the top of a 2.5×28.5 cm column (140 ml bed volume) of resin and eluted with methanol (210 ml) collecting 60 fractions, each 3.5 ml. Activity was recovered in fractions 13 through 24.

Gel filtration of the methanol-soluble fraction was performed on Sephadex LH-20 in methanol. The sample was applied in a minimal volume of methanol to the top of a 2.5×28.5 cm column of resin and eluted with methanol (210 ml) collecting 60 fractions, each 3.5 ml. Activity was recovered in fractions 13 through 22.

As a thin-layer chromatographic comparison of the active fractions from the two gel filtration experiments indicated that they were similar in composition, the active fractions from both experiments were pooled and concentrated. Gel filtration was again performed on Sephadex LH-20 in methanol. The sample was applied in a minimal volume of methanol to the top of a 2.5×28.5 cm column of resin and eluted with methanol (210 ml), collecting 60 fractions, each 3.5 ml. Activity was recovered in fractions 15 through 22 with some tailing into later fractions.

Fractions 15 through 22 were pooled, evaporated to dryness, and redissolved in ethyl acetate:methanol (1:2 v/v, 3 ml). Partition chromatography was then performed on this sample using a column (150 ml bed volume) of Sephadex LH-20 preswollen in methanol and equilibrated with ethyl acetate:methanol (99:1 v/v).

The sample was applied to the top of the column and eluted successively with the following solvent mixtures:

| Ethyl | acetate:methanol | (99:1 v/v) | 300 ml |
|---|---|---|---|
| Ethyl | acetate:methanol | (19:1 v/v) | 250 ml |
| Ethyl | acetate:methanol | (9:1 v/v) | 200 ml |
| Methanol | | | 1000 ml |

Two hundred fractions, each 7.5 ml, were collected, followed by a wash fraction. The main zone of activity eluted in fractions 85 through 112, with a minor zone eluting in fractions 17 through 36.

Fractions 85 through 112 were pooled, evaporated, and redissolved in methanol (2 ml). Partition chromatography was then performed on the sample, using a column of Sephadex LH-20 (300 ml bed volume) preswollen in methanol and equilibrated with ethyl acetate:methanol (19:1 v/v). The sample was applied to the top of the column and eluted successively with the following solvent mixtures:

| Ethyl acetate:methanol | (19:1 v/v) | 500 ml |
|---|---|---|
| Ethyl acetate:methanol | (9:1 v/v) | 300 ml |
| Ethyl acetate:methanol | (3:1 v/v) | 300 ml |
| Methanol | | 500 ml |

Two hundred fractions, each 8 ml, were collected, with activity being recovered in a broad zone in fractions 26 through 110.

Fractions 26 through 110 were pooled, evaporated to dryness, and redissolved in methanol (6 ml). Preparative, reverse-phase, high-performance liquid chromatography (HPLC) was performed on a Lichrosorb RP-18 column (EM Reagents, 5 micron particle size, 10×250 mm) operated at ambient temperature with the following solvent gradient delivered at 4.7 ml/min:

| 0–2 minutes | water |
|---|---|
| 2–6 minutes | linear gradient from water to water:acetonitrile (9:1 v/v) |
| 6–8 minutes | linear gradient from water:acetonitrile (9:1 v/v) to water:acetonitrile (4:1 v/v). |
| 8–28 minutes | linear gradient from water to water:acetonitrile (4:1 v/v) to water acetonitrile (1:1 v/v) |
| 28–48 minutes | linear gradient from water:acetonitrile (1:1 v/v) to acetonitrile |
| 48–60 minutes | acetonitrile |

Thirteen such runs were performed, and 60 fractions, each one minute in duration, were collected in each run. Activity was recovered in fractions eluting between 25 and 33 minutes.

The active fractions were pooled, evaporated to dryness, and redissolved in methanol (1 ml). Isocratic, preparative, reverse-phase HPLC was performed on the sample using a Lichrosorb RP-18 column (10×250 mm, 5 micron particle size) at ambient temperature, eluted with water:acetonitrile (3:2 v/v) at 4.7 ml/min. Five runs were made, collecting 60 fractions, each one minute in duration, per run. Three zones of activity were observed, eluting in fractions from 9 to 13 minutes, 14 to 19 minutes and 27 to 30 minutes.

Repetitive preparative HPLC of the fraction eluting from 14 to 15 minutes, using the same column and operating conditions, afforded the compound of Formula Ia (1 mg) as a white solid. Analytical HPLC, using a Lichrosorb R-18 column (4.0×250 mm, 5 micron particle size) eluted with water:acetonitrile (3:2) at 2 ml/min, indicated a retention time of 7.0 minutes.

Repetitive preparative HPLC of the fraction eluting from 16 to 17 minutes, using the same column and operating conditions, afforded the compound of Formula Ib (2 mg) as a white solid. Analytical HPLC, using a Lichrosorb RP-18 column (4.0×250 mm, 5 micron particle size) eluted with water acetonitrile (3:2 v/v) at 2 ml/min, indicated a retention time of 7.7 minutes.

Characterization of the Compounds of Formula I

The solid materials obtained in Example 2 were characterized by high resolution mass spectrometry and nuclear magnetic resonance spectroscopy (i.e. proton and carbon-13) as discussed below.

Mass Spectral Data

The mass spectra were recorded on a Finnigan Mat212 instrument by electron impact at 90 eV. Trimethylsilyl derivatives (TMS) were prepared with a 1:1 mixture of BSTFA-pyridine at room temperature. Exact mass measurements were made on the same instrument at high resolution by the peak matching method using perfluorokerosene (PFK) as internal standard. The FAB spectra were obtained on a Mat731 instrument.

Table 1 summarizes the low resolution mass spectral data. In all cases the molecular ion was confirmed by FAB-MS. High resolution data was obtained only on compound Ia and is given in Table II.

NMR Data

NMR data were obtained on a Varian XL-400 NMR spectrometer in $CD_3OD$ at ambient room temperature. Chemical shifts are given relative to tetramethylsilane at zero ppm using the solvent peak as standard at $\delta 3.30$ in $^1H$ NMR spectra and at 49.0 ppm for $^{13}C$ NMR spectra. Only $^{13}C$ NMR data are provided for compound Ia.

$^{13}C$ NMR Chemical Shifts

In agreement with the molecular Formula $C_{34}H_{52}O_{10}$, 34 carbon atoms are observed in the spectrum of compound Ia with the following chemical shifts: 12.6, 13.2, 21.1, 23.5, 26.2, 26.8, 29.3, 29.5, 35.7, 41.2, 41.4, 43.3, 44.9, 45.1, 45.4, 46.3, 49.9, 56.0, 57.1, 62.6, 68.1, 72.4, 73.22, 73.28, 75.3, 78.2, 83.5, 88.0, 101.0, 116.9, 127.3, 138.8, 141.8, 176.3 ppm.

1H NMR Spectra

Figure 2:
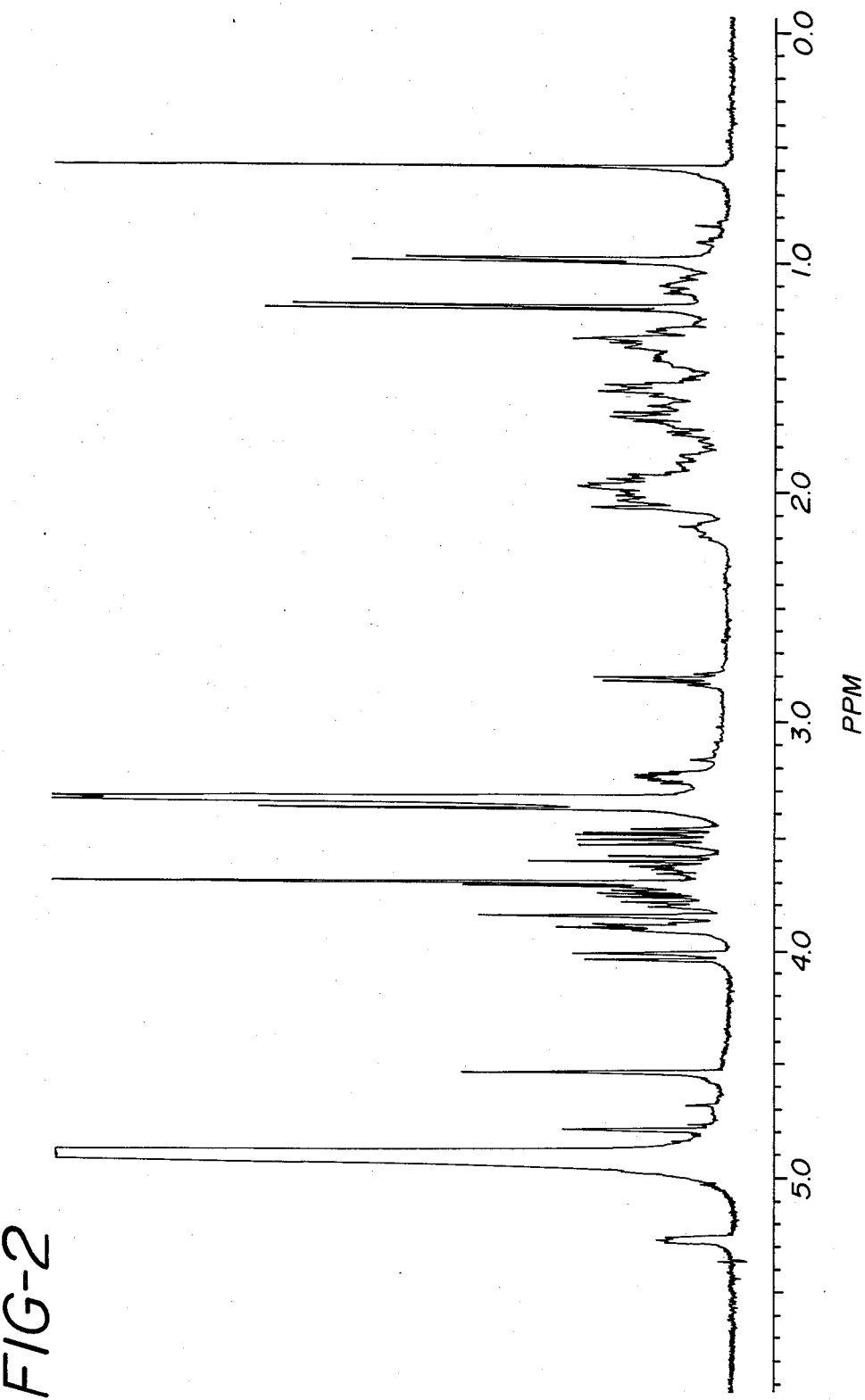
FIG. 2 is a ($^1$H-NMR) spectrum of compound Ib.

The spectra of compounds Ia and Ib are shown in FIGS. 1 and 2.

TABLE I

| Low Resolution Mass Spectral Data | | | | |
|---|---|---|---|---|
| COMPOUND | M+ | TMS | AGLYCONE | TMS |
| Ib | 652 | 6 | 472 | 2 |
| Ia | 620 | 5 | 440 | 1 |

TABLE II

| High Resolution Mass Spectral Data for Compound Ia | | | |
|---|---|---|---|
| FOUND | CALCULATED | FORMULA | ASSIGNMENT |
| 440.2943 | 440.2927 | $C_{28}H_{40}O_4$ | $M+ - C_6H_{12}O_6$ (MANNOSE) |
| 285.1859 | 285.1854 | $C_{19}H_{25}O_2$ | AGLYCONE - $C_9H_{15}O_2$ |

On a basis of these and other data, the structures were assigned.

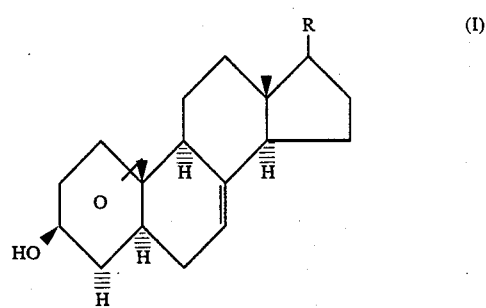

(I)

wherein R is

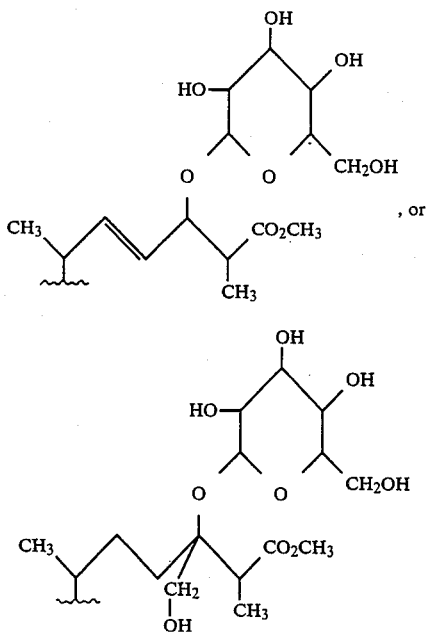

The structures shown above encompass all possible stereoisomers.

EXAMPLE 3

In Vitro Activity of the Compounds of Formula I

The following is a method for assessing testosterone-5α-reductase inhibitory activity. The microsomal fraction of rat liver is used as an enzyme source because of the relative ease of preparation of this enzyme. Human prostate enzyme was also used to evaluate the compounds of formula I.

A. Enzyme Preparation

The enzyme was prepared from rat liver microsomal fractions. Ten rat livers were obtained from male Wistar rats (for less glycogen, starved overnight), sacrificed by decapitation.

The livers were then placed in ice cold phosphate buffered saline solution and rinsed twice to remove excess blood and minced on ice in a beaker into small pieces with scissors. Five ml of buffer per gram of tissue was added to the minced tissue and the tissue was homogenized for 10 seconds using a Brinkman polytron at setting #4. An equal olume of buffer was added and the homogenate was centrifuged at 10,000 xg for 10 minutes. The pellet was discarded.

The supernatant was centrifuged at 100,000 xg for 30 minutes (Beckman Model L5-50 Ultracentrifuge). The supernatant was discarded and the pellets were resuspended in half the original volume of phosphate buffered saline and rehomogenized at setting #4 for 5 seconds. The homogenate was centrifuged at 100,000 xg again for 20 minutes.

The pellet was suspended in ice cold assay buffer at 100 μl protein per ml. (Protein measurement was as described in "Methods", below). One ml of solution was pipetted to each vial and stored in a liquid nitrogen freezer. The enzyme is stable for at least 4 months.

When ready for assay, one vial of enzyme was further diluted with ice cold assay buffer containing 1 mg/ml of BSA (prepared by dissolving 10 mg of BSA in 10 ml of assay buffer) to a final enzyme protein concentration between 2 to 7 μg/ml.

B. Methods

The protein concentration of enzyme was estimated by a spectrophotometric method as described by Groves et. al., (5). Each 0.4 optical adsorbance difference between 224 nm and 233 nm is equal to 0.1 mg of protein per ml.

One ml of methanol was added to 1 ml of fermentation rroth including mycelia in a 13×100 mm test tube and the tube was vortexed for 10 seconds and centrifuged at 1520 xg for 10 minutes in a Beckman TJ-6 table top centrifuge. Ten μl of each supernatant was used directly for the assay.

Ten μl of the above methanol extract of each broth being tested was added to a 13×100 mm test tube as was 100 μl of enzyme and 100 μ $^3$H-testosterone working solution. The tube was mixed gently and incubated at 37° C. for 20 minutes.

One ml of water saturated ethylacetate was then added immediately to the tube and vortexed. A blank was run by adding enzyme after ethylacetate was added. An enzyme control was run with 10 μl of 50% methanol. Positive control was run with 10 μl of inhibitor instead of 50% methanol extract. All the blanks, enzyme controls, and inhibitors were run in duplicate.

The tubes were then centrifuged at 1520 xg for 5 minutes in a Beckman TJ-6 table top centrifuge. 0.8 ml of organic phase (upper layer) was transferred to a separate tube and was dried under vacuum in a speed vac concentrator (Savant Co.).

Fifty μl of the spike solution was added to each dried tube and the tube was tapped gently and 25 μl of this solution was spotted onto Whatman LK6DF TLC plates. The plates were developed in a 50% ethylacetate and 50% cyclohexane solvent system until the solvent had traveled three quarters of the way up the plate.

The plates were placed under short U.V. light. Two distinct bands are visible. These represent the Rf values for androstenedione and testosterone. The plates are scored with a razor blade between the two bands and approximately 3 cm above the uppermost band and below the lower band. The zones containing these two bands are scraped off into a separate counting vial via a glass funnel and counted in 10 ml of scintillation cocktail for 10 minutes.

The uppermost band (band 1) which contains the labeled $^3$H-dihydrotestosterone as converted from $^3$H-testosterone via the 5α-reductase is a measure of enzyme activity. The enzyme activity is expressed as percent conversion of testosterone to dihydrotestosterone.

$$\% \text{ Conversion} = \frac{CPM_{band\ 1}}{CPM_{band\ 1} + CPM_{band\ 2}} \times 100$$

Δ% Conversion =

% Conversion Control or Broth − % Conversion Blank Avg.

% Inhibition of broth extract or inhibitor =

$$100 \times \frac{\Delta\% \text{ conversion control avg} - \Delta\% \text{ conversion broth ext. or inhibitor}}{\Delta\% \text{ conversion control avg}}$$

C. Results

The compounds of Formula I were found highly active in the testosterone 5α-reductase enzyme inhibition assay. One hundred percent inhibition was observed with 50 μl of 50% aqueous methanol extract of the whole broth. The IC$_{50}$ was estimated to be 1.5 μl broth per ml of assay mixture. The active component was found to be methanol soluble. The purified components of the compounds of Formula I were evaluated against both rat liver enzyme and human prostate enzyme inhibition assays. The IC$_{50}$ of this purified component against rat liver enzyme was estimated to be 0.8 ng/ml and the IC$_{50}$ of this purified component against human prostate enzyme was estimated to be 5 μg/ml. The human prostate enzyme was prepared as described in the next Example.

EXAMPLE 4

In Vitro Inhibition in Human Prostate Tissue

A. Procedure

A 1.8 gram slice of human prostate was thawed, minced and homogenized in 0.25M sucrose buffer. The homogenate was centrifuged at 1200 RPM for 10 minutes and the supernate was discarded. After washing the pellet 3 times in buffer, it was suspended in buffer so that 1.0 ml contained about 300 mgs of homogenized tissue. 0.1 ml of this suspension was incubated with 0.01 ml of inhibitor and 0.1 ml of a mix containing $^3$H-testosterone, unlabeled testosterone and dihydrotestosterone, glucose-6-phosphate, glucose-6-phosphate dehydrogenase and NADP for 30 minutes at 37° C. After the incubation, the steroids were extracted with 3.0 ml ethyl acetate, the organic phase was separated and dried down under N$_2$. This extract was spotted onto TLC plates. After developing the TLC plates in ethyl acetate:cyclohexane 1:1, the $^3$H-DHT zone was scraped from the plate and counted.

B. Results

An excellent dose response was obtained with the compounds of Formula I. An IC$_{50}$ was calculated to be about 5 μg/ml. The results are shown in TABLE 2, below:

TABLE 2

| | Dose (ng/tube) | Time of Incubation (min) | H$^3$—DHT (cpm) | H$^3$DHT (% Inhibition) of DHT formation |
|---|---|---|---|---|
| Component A & B | 5000 | 30 | 2039 | 69.1 |
| | 1000 | 30 | 3311 | 48.8 |
| | 200 | 30 | 4549 | 29.2 |
| | 40 | 30 | 5433 | 15.1 |
| | 8 | 30 | 5694 | 11.0 |
| | 1.6 | 30 | 6054 | 5.3 |
| | — | 30 | 6386 | — |

The ability of the compound of Formula I to inhibit testosterone-5α-reductase makes these compounds useful as pharmaceutical agents. These compounds will be especially useful in the treatment and prevention of disease states wherein testosterone-5α-reductase is involved, such as, for example, acne seborrhea, female hirsutism and benign prostate hypertrophy.

The compounds of Formula I, or pharmaceutically acceptable salts thereof, can be administered to a human subject either alone, or preferably, in combination with pharmaceutically acceptable carriers or diluents, in pharmaceutically acceptable carriers or diluents in a pharmaceutical practice. The compound can be administered orally or parenterally. Parenteral administration includes intravenous, intramuscular, intraperitoneal, subcutaneous and topical administration.

For oral use of compound of this invention, the selected compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspension are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When the compounds of Formula I or salts thereof is used as an inhibitor of testosterone 5α-reductase in a human subject, the daily dosage will normally be determined by the prescribing physician. Moreover, the dosage will vary according to the age, weight and response of the individual patient, as well as the severity of the patient's symptoms. However, in most instances, an effective daily dosage will be in the range from about 1 mg to about 1500 mg and preferably 10 mg to 500 mg in a single or divided doses. On the other hand, it may be necessary to use dosages outside these limits in some cases.

What is claimed is:

1. A compound of Formula I:

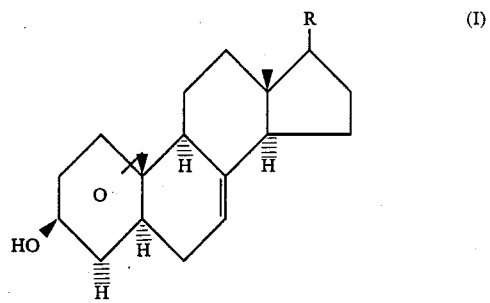

wherein R is

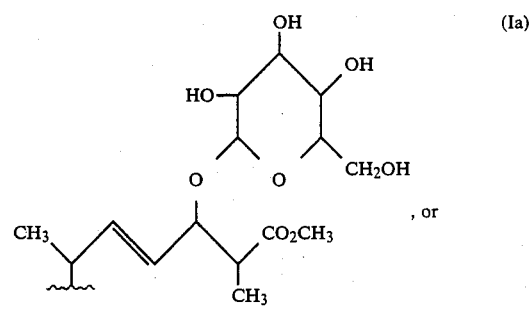

, or

-continued

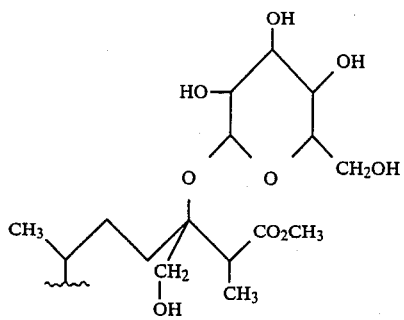
(Ib)

or the pharmaceutically acceptable salts thereof.

2. A compound according to claim 1, having the empirical formula $C_{34}H_{52}O_{10}$ and the NMR spectrum of FIG. 1.

3. A compound according to claim 1 having the empirical formula $C_{35}H_{56}O_{11}$ and the NMR spectrum of FIG. 2.

4. A process for producing a testosterone 5alpha-reductase inhibitor compound which comprises growing the strain of Gliocladium ATCC No. 20826 in an aqueous nutrient medium by aerobic fermentation of an assimilable carbon and nitrogen source and recovering therefrom a compound according to claim 1.

5. A mixture of the compounds of claim 1 produced by controlled aerobic fermentation of a fungus of the genus Gliocladium in an assimilable carbon and nitrogen source.

6. A mixture of claim 5, wherein the fungus is ATCC No. 20826.

* * * * *

UNITED STATES PATENT AND TRADEMARK OFFICE
CERTIFICATE OF CORRECTION

PATENT NO. : 4,814,324
DATED : MAR. 21, 1989
INVENTOR(S) : BORRIS, BURG, HENSENS, HUANG, KELEMEN & MOCHALES

It is certified that error appears in the above-identified patent and that said Letters Patent is hereby corrected as shown below:

Please correct the Formula I structure in columns 2, 8, and 12 to the bridge oxygen atom.

should read:

-- 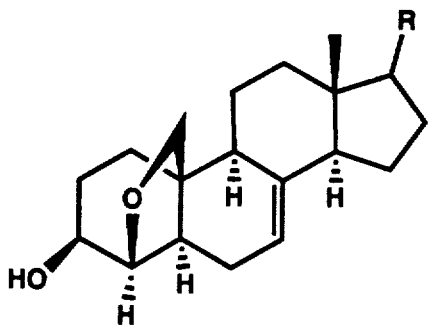 --

Signed and Sealed this

Thirty-first Day of October, 1989

*Attest:*

DONALD J. QUIGG

*Attesting Officer*     *Commissioner of Patents and Trademarks*